United States Patent [19]

Wu

[11] Patent Number: 5,131,536

[45] Date of Patent: Jul. 21, 1992

[54] COTTONBUD CASE

[76] Inventor: Ching-Kao Wu, Room 2, 11th Fl., No. 85, Shoei-Yuan Road, Taipei, Taiwan

[21] Appl. No.: 746,369

[22] Filed: Aug. 16, 1991

[51] Int. Cl.⁵ .................. B65D 83/02; B65D 25/38
[52] U.S. Cl. .................................. 206/362; 206/267; 206/256
[58] Field of Search .............. 206/362, 267, 256

[56] References Cited

U.S. PATENT DOCUMENTS 3,056,493  10/1962  Berryman et al. ............... 206/362
3,759,375  9/1973  Nappi ................................. 206/362
3,976,195  8/1976  Cohen ............................... 206/362
4,236,637  12/1980  Castner, Sr. et al. ............ 206/362
4,989,730  2/1991  Lemoine .......................... 206/362

FOREIGN PATENT DOCUMENTS 2048218  12/1980  United Kingdom ............ 206/362

Primary Examiner—William I. Price

[57] ABSTRACT

A cottonbud case having a lid and a case body provided with a plurality of rooms for storing cottonbuds horizontally and middle portions of the rooms being vacant for fingers to insert to put in or pick up cottonbuds so as to keep clean cotton balls at both ends of sticks.

1 Claim, 4 Drawing Sheets

[FIG. 1]

(PRIOR ART)

COTTONBUD CASE

BACKGROUND OF THE INVENTION

A conventional cottonbud or swab case as shown in FIG. 1 has a cylindrical container 10 closed with a lid 11, which may often be taken off with excessive force by a user as to force some of the cottonbuds stored therein to drop out of the container 10. In addition, extra cottonbuds may be carelessly and easily pulled out together with the one chosen to be picked up. And if worse, the cotton balls at both ends of sticks may be polluted in picking up. Spreading-out upper ends of the cottonbuds should be pushed to stand upright before the lid 11 is to be covered on the container 10, which is quite inconvenient to handle in covering the lid 11 everytime it is taken off in picking out a cottonbud.

SUMMARY OF THE INVENTION

In view of the disadvantage of a conventional cottonbud or swab case mentioned above, this invention has been devised to supply a cottonbud case, wherein its interior cavity is divided into a plurality of rooms for storing cottonbuds horizontally and lengthwise. The rooms are divided into three portions, two side ones and a middle one, and two side portions are for the cotton balls at both ends of a stick to lie in and the middle portion for the middle section of cottonbuds to lie in and for fingers to put in or take out cottonbuds. Thus the cotton balls at both ends of sticks can be kept clean without contaminated by fingers.

The cottonbud case in the present invention has been planned to have the following advantages.

1. It is convenient to store cottonbuds horizontally and to pick up one by one easily by fingers catching hold of the middle section of a cottonbud.

2. In picking up the cottonbuds stored in it, the cotton balls at both ends of a stick can never be touched by fingers to be contaminated.

DETAILED DESCRIPTION OF THE INVENTION

Figure 1:
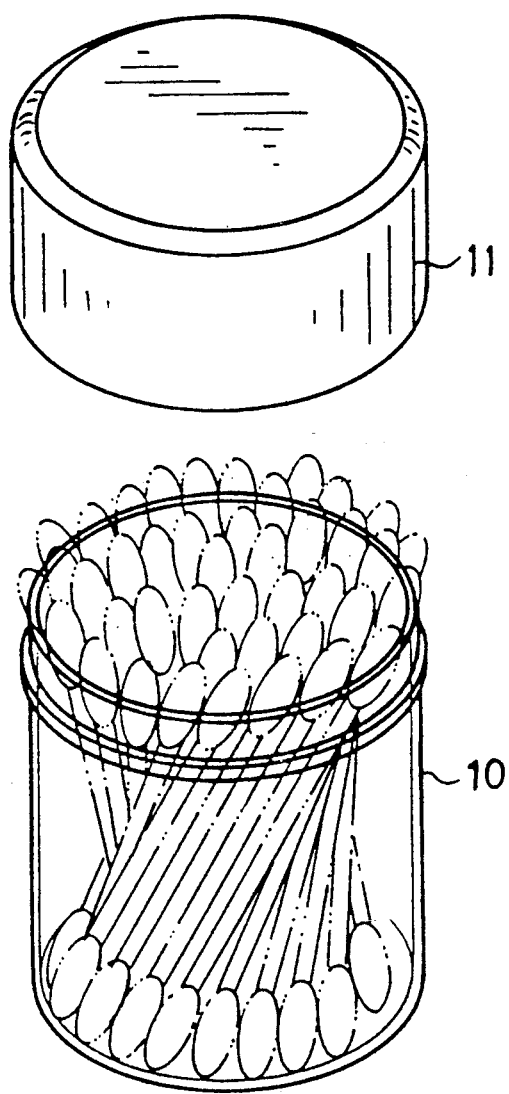
FIG. 1 is a perspective view of a conventional cottonbud case.
Figure 2:
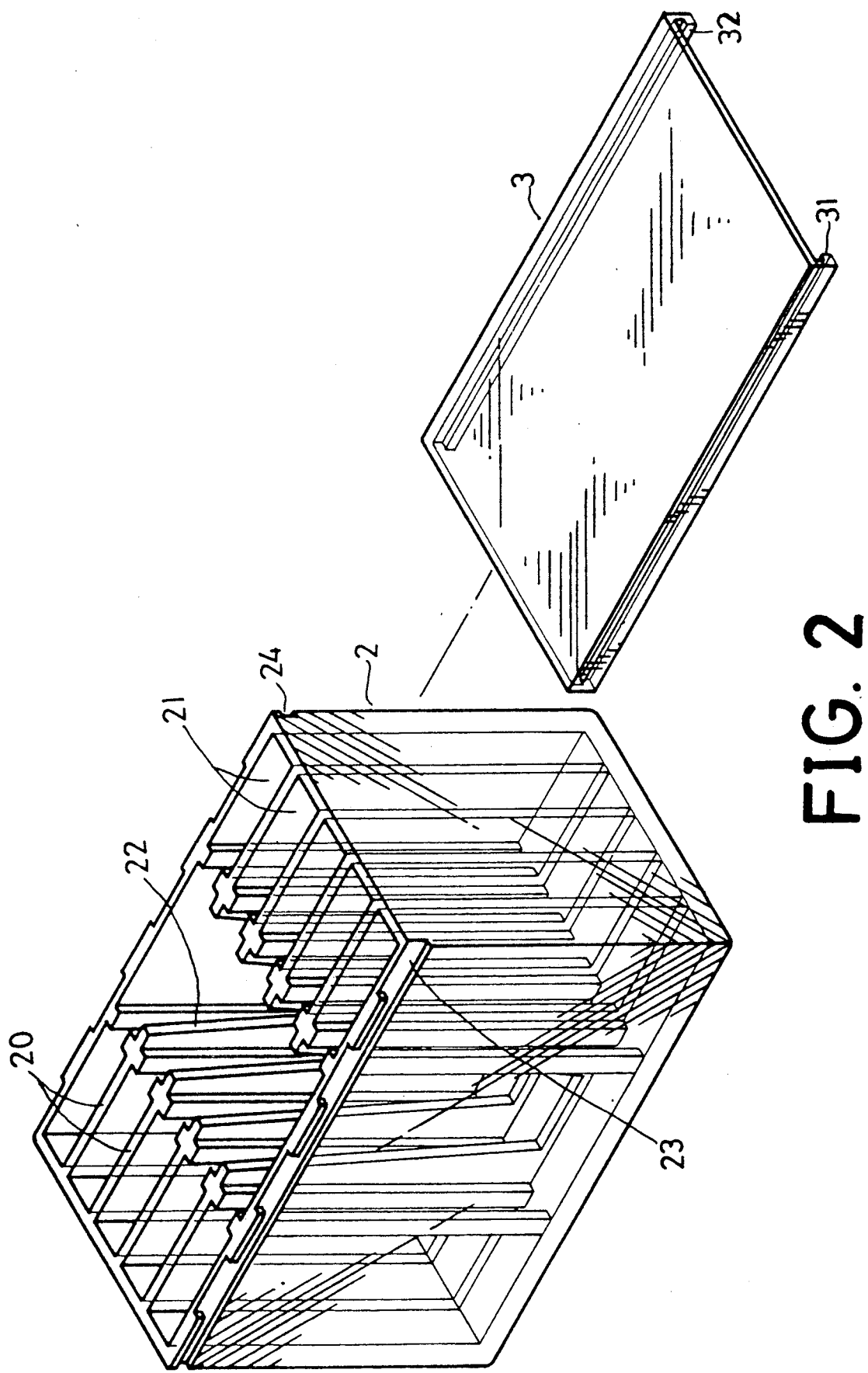
FIG. 2 is an exploded perspective view of a cottonbud case in accordance with the present invention.
Figure 3:
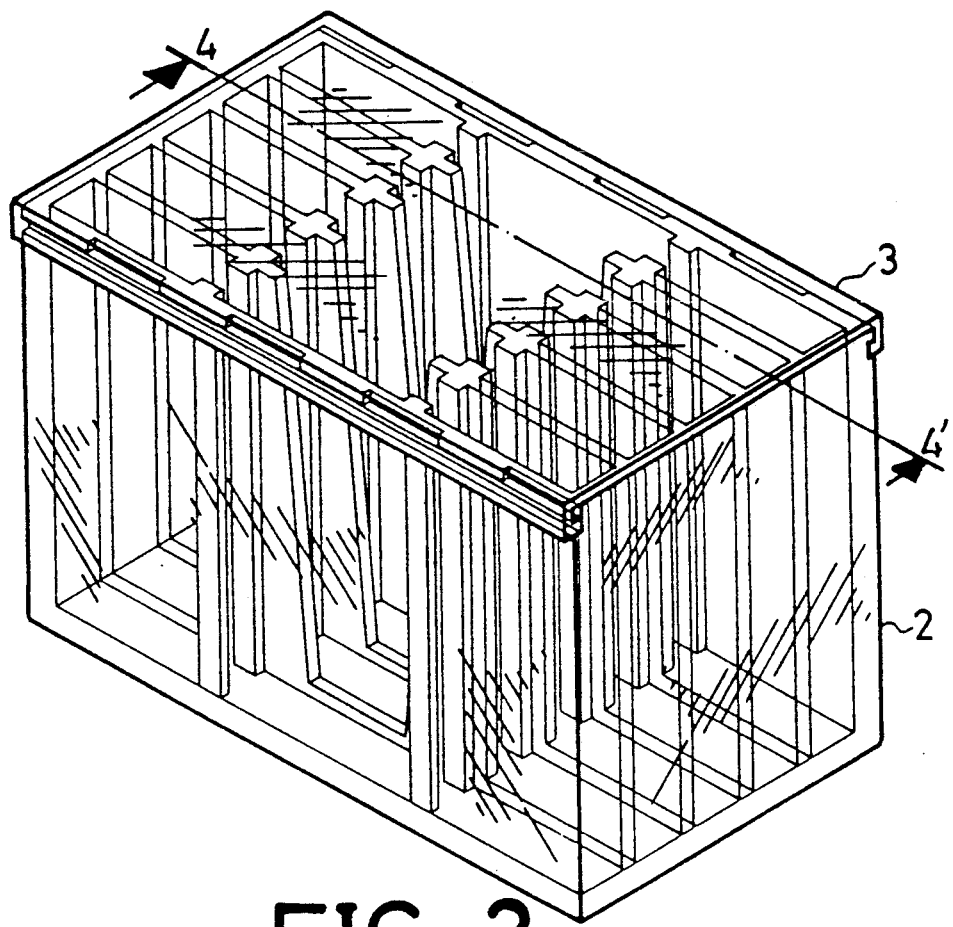
FIG. 3 is a perspective view of a cottonbud case in accordance with the present invention.

A cottonbud or swab case in accordance with the present invention, as shown in FIG. 2, comprises a rectangular case body 2 and a lid 3 as the main components.

The rectangular case body 2 has its interior cavity divided with a plurality of parallel vertical boards 20 equally spaced apart to form a plurality of lengthwise rooms 21, each of which consists of two side portions for cotton balls at both ends of sticks to lie in and a middle open portion 22 for fingers to put in or take out cottonbuds at the middle sections so that cotton balls at both ends of sticks can never be contaminated by fingers in picking up or putting in. The case body 2 is also provided with two guide grooves 23, 24 at both lengthwise upper sides for two projecting ridges 31, 32 on both lengthwise sides of the lid 3 to fit therein so as to keep said lid 3 securely covered on said case body 2.

Figure 4:
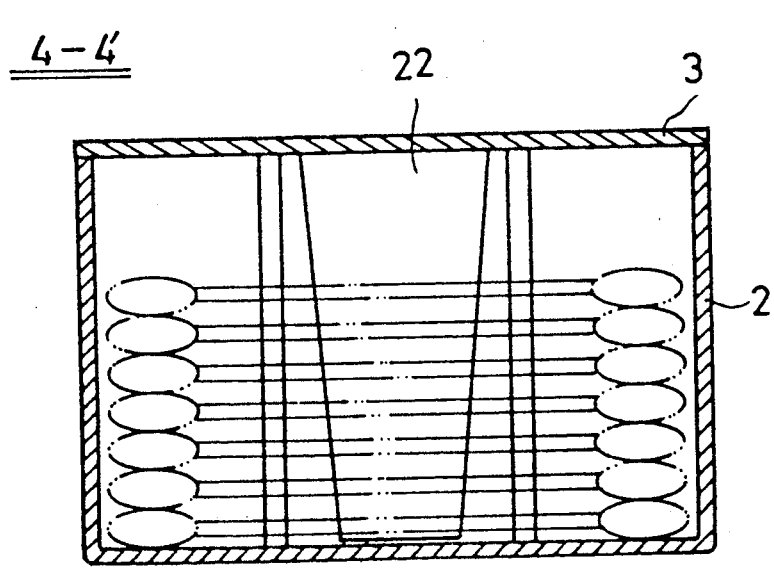
FIG. 4 is a cross-sectional view of a cottonbud case in accordance with the present invention.
Figure 5:
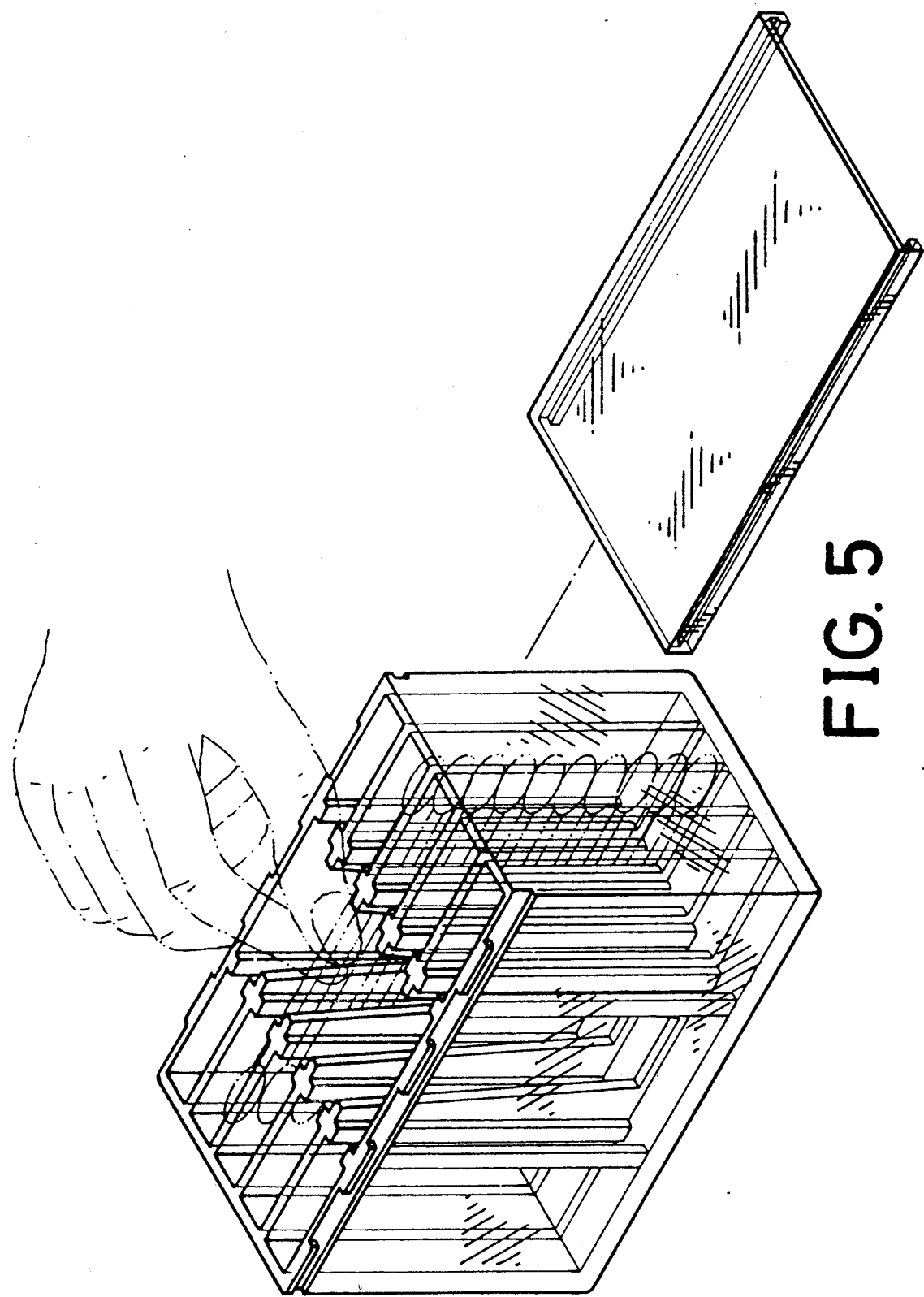
FIG. 5 is a perspective view of a hand picking up a cottonbud from the cottonbud case in accordance with the present invention.

In using this cottonbud case, the lid 3 is to be pulled open slidably, with the ridges 31, 32 moving in the guide grooves 23, 24, and then cottonbuds are to be horizontally laid in the rooms 21. In picking up the cottonbuds, they are to be picked up by fingers inserting in the middle portion 22 of the room 21 without touching to contaminate both cotton balls at both ends as shown in FIGS. 4 and 5.

What is claimed is:

1. A cottonbud case comprising a case body and a lid to cover the case body, said case body having its interior cavity divided into a plurality of rooms consisting of two side portions and a middle portion for storing cottonbuds horizontally with both ends laid in the side portions, said middle portion being for fingers to insert to put in or pick up cottonbuds, said case body also having a guide groove at both upper lengthwise side edges for the lid to close or open the case body by sliding horizontally by means of two projecting ridges provided at the lengthwise sides of the lid and moving in said guide grooves in the case body.

* * * * *